(12) United States Patent
Gullberg et al.

(10) Patent No.: US 10,465,235 B2
(45) Date of Patent: Nov. 5, 2019

(54) MULTIPLEXED PROXIMITY LIGATION ASSAY

(75) Inventors: Mats Gullberg, Sollentuna (SE); Ola Söderberg, Österbybruk (SE); Ulf Landegren, Uppsala (SE); Yanling Liu, Uppsala (SE)

(73) Assignee: NAVINCI DIAGNOSTICS AB, Uppsala (SE)

(*) Notice: Subject to any disclaimer, the term of this patent is extended or adjusted under 35 U.S.C. 154(b) by 466 days.

(21) Appl. No.: 14/119,925

(22) PCT Filed: May 23, 2012

(86) PCT No.: PCT/EP2012/059571
§ 371 (c)(1),
(2), (4) Date: Feb. 24, 2014

(87) PCT Pub. No.: WO2012/160083
PCT Pub. Date: Nov. 29, 2012

(65) Prior Publication Data
US 2014/0194311 A1   Jul. 10, 2014

(30) Foreign Application Priority Data

May 24, 2011   (GB) .................................. 1108678.2

(51) Int. Cl.
*C12Q 1/68* (2018.01)
*C12Q 1/6837* (2018.01)
(Continued)

(52) U.S. Cl.
CPC ........... *C12Q 1/6837* (2013.01); *C12Q 1/682* (2013.01); *C12Q 1/6804* (2013.01)

(58) Field of Classification Search
None
See application file for complete search history.

(56) References Cited

U.S. PATENT DOCUMENTS 6,878,515 B1   4/2005   Landegren
7,306,904 B2   12/2007  Landegren et al.
(Continued)

FOREIGN PATENT DOCUMENTS

WO   01/61037 A1    8/2001
WO   2007/107743 A1   9/2007
(Continued)

OTHER PUBLICATIONS

Soderberg et al. (Nature Methods, 2006, 3(12):995-1000).*
(Continued)

*Primary Examiner* — Stephanie K Mummert
(74) *Attorney, Agent, or Firm* — Porter Wright Morris & Arthur LLP

(57) ABSTRACT

The present invention provides a method for detecting interactions between or with any two of at least three target substrates, or any two of at least three features of a target substrate, or a combination of interactions and features of target substrates, by a multiplexed proximity ligation assay, said method comprising: a) for each of the at least three target substrates or features, providing a proximity probe comprising a binding moiety with affinity for the feature or binding site on said substrate, and a proximity probe oligonucleotide coupled on the binding moiety; wherein each of the proximity probe oligonucleotide carries a unique tag sequence; b) mixing the proximity probes with a sample, under a condition to allow binding of each proximity probe to its respective binding site or feature on each of said substrates through the binding moiety, c) simultaneous with, or following step b), forming circularized DNA molecules where any two proximity probes bind sufficiently close to each other on the substrate, wherein each of the circularized DNA molecules comprise complementary sequences to the unique tag sequences from the two proximity probes oligo- (Continued)

nucleotides; d) amplifying the circularized DNA; and e) characterizing the amplified DNA.

21 Claims, 9 Drawing Sheets

Specification includes a Sequence Listing.

(51) Int. Cl.
C12Q 1/6804 (2018.01)
C12Q 1/682 (2018.01)

(56) References Cited

U.S. PATENT DOCUMENTS

| | | | |
|---|---|---|---|
| 8,481,698 B2 * | 7/2013 | Lieberman | G01N 33/5308 536/23.1 |
| 8,580,504 B2 * | 11/2013 | Fredriksson | C12Q 1/6804 435/6.12 |
| 9,228,228 B2 * | 1/2016 | Drmanac | C12Q 1/6809 |
| 2002/0064779 A1 | 5/2002 | Landegren et al. | |
| 2004/0248103 A1 | 12/2004 | Feaver et al. | |
| 2008/0261204 A1 | 10/2008 | Lexow | |

FOREIGN PATENT DOCUMENTS

| | | |
|---|---|---|
| WO | 2007/117444 A2 | 10/2007 |
| WO | 2008/016644 A1 | 2/2008 |
| WO | 2012/049316 A1 | 4/2012 |
| WO | 2012/057689 A1 | 5/2012 |

OTHER PUBLICATIONS

Leuchowius et al. (Molecular Diagnostics, 2010, chapter 20, p. 299-306) (Year: 2010).*
Söderberg et al, Nature Methods, 3(12):995-1000 (2006).
Leuchowius et al, Molecular Diagnostics, Second Edition, 299-306 (Jan. 1, 2010).
Leuchowius et al, Cytometry Part A, 75A(10):833-839 (2009).
Schallmeiner et al, Nature Methods, 4(2):135-137 (2007).
Weibrecht et al, Expert Review of Proteomics, 7(3):401-409 (Jun. 1, 2010).
Gustafsdottir et al, Analytical Biochemistry, 345(1):2-9 (2005).
Söderberg et al, Methods: A Companion to Methods in Enzymology, 45(3):227-232 (2008).
Melin et al, New Biotechnology, 25(1):42-48 (2008).
Leuchowius et al, Molecular & Cellular Proteomics, 9(1):178-183 (Jan. 1, 2010).
Gustafsdottir et al, Proximity ligation assays for sensitive and specific protein analyses, Analytical Biochemistry, vol. 345, pp. 1-9 (2005).
Schallmeiner et al, Sensitive protein detection via triple-binder proximity ligation assays, Nature Methods, 4(2):135-137 (2007).
Soderberg et al, Direct observation of individual endogenous protein complexes in situ by proximity ligation, Nature Methods, vol. 3, No. 12, pp. 995-1000 (2006).
Jarvius et al, In Situ Detection of Phosphorylated Platelet-derived Growth Factor Receptor β Using a Generalized Proximity Ligation Method, Molecular & Cellular Proteomics, 6(9): 1500-1509 (2007).
Ericsson et al, A dual-tag microarray platform for high-performance nucleic acid and protein analyses, Nucleic Acids Research, vol. 36, No. 8, e45 (nine pages) (2008).
Melin et al, Ligation-based molecular tools for lab-on-a-chip devices, New Biotechnology, vol. 25, No. 1, pp. 42-48.
Soderberg et al, Characterizing proteins and their interactions in cells and tissues using the in situ proximity ligation assay, Methods, vol. 45(3): 227-232 (2008).
Leuchowius et al, Flow Cytometric In Situ Proximity Ligation Analyses of Protein Interactions and Post-translational Modification of the Epidermal Growth Factor Receptor Family, Cytometry Part A, vol. 75A, pp. 833-839 (2009).
Leuchowius et al, High Content Screening for Inhibitors of Protein Interactions and Post-translational Modifications in Primary Cells by Proximity Ligation, Molecular & Cellular Proteomics, 9(1): 178-183 (Jan. 2010) (Online Oct. 27, 2009).
Weibrecht et al, Proximity ligation assays: a recent addition to the proteomics toolbox, Expert Reviews Proteomics, 7(3): 401-409 (Jun. 2010).
Leuchowius et al, Protein Diagnostics by Proximity Ligation: Combining Multiple Recognition and DNA Amplification for Improved Protein Analyses, Molecular Diagnostics, Chapter 20, pp. 299-306 (2010).

* cited by examiner

```
                        SEQUENCE LISTING

<160> NUMBER OF SEQ ID NOS: 16

<210> SEQ ID NO 1
    <211> LENGTH: 22
    <212> TYPE: DNA
    <213> ORGANISM: ARTIFICIAL SEQUENCE
    <220> FEATURE:
    <223> OTHER INFORMATION: Oligo 1

<400> SEQUENCE: 1
gacgctaata gttaagacgc tt                                              22

<210> SEQ ID NO 2
    <211> LENGTH: 52
    <212> TYPE: DNA
    <213> ORGANISM: ARTIFICIAL SEQUENCE
    <220> FEATURE:
    <223> OTHER INFORMATION: Oligo 2

<400> SEQUENCE: 2
aaaaaaaaaa tatgacagaa ccgggcgaca taagcagata ctagacactc tt            52

<210> SEQ ID NO 3
    <211> LENGTH: 52
    <212> TYPE: DNA
    <213> ORGANISM: ARTIFICIAL SEQUENCE
    <220> FEATURE:
    <223> OTHER INFORMATION: Oligo 3

<400> SEQUENCE: 3
aaaaaaaaaa tatgacagaa catacggtct cgcagatcgc ttagacactc tt            52

<210> SEQ ID NO 4
    <211> LENGTH: 52
    <212> TYPE: DNA
    <213> ORGANISM: ARTIFICIAL SEQUENCE
    <220> FEATURE:
    <223> OTHER INFORMATION: Oligo 4

<400> SEQUENCE: 4
aaaaaaaaaa tatgacagaa cggacgatca tccagcacta gtagacactc tt            52

<210> SEQ ID NO 5
    <211> LENGTH: 27
    <212> TYPE: DNA
    <213> ORGANISM: ARTIFICIAL SEQUENCE
    <220> FEATURE:
    <223> OTHER INFORMATION: Oligo 5
```

<400> SEQUENCE: 5
agacgctaat agttaagacg cttauuu                                          27

<210> SEQ ID NO 6
<211> LENGTH: 65
<212> TYPE: DNA
<213> ORGANISM: ARTIFICIAL SEQUENCE
<220> FEATURE:
<223> OTHER INFORMATION: Circularisation Oligo 1

<400> SEQUENCE: 6
ctattagcgt ccagtgaatg cgagtccgtc taagagagta gtacagcagc cgtcaagagt      60
gtcta                                                                  65

<210> SEQ ID NO 7
<211> LENGTH: 25
<212> TYPE: DNA
<213> ORGANISM: ARTIFICIAL SEQUENCE
<220> FEATURE:
<223> OTHER INFORMATION: Circularisation Oligo 2

<400> SEQUENCE: 7
gttctgtcat atttaagcgt cttaa                                            25

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: tag specific oligo 1

<400> SEQUENCE: 8
agcgatctgc gagaccgtat                                                  20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: tag specific oligo 2

<400> SEQUENCE: 9
ctagtgctgg atgatcgtcc                                                  20

<210> SEQ ID NO 10
<211> LENGTH: 20
<212> TYPE: DNA
<213> ORGANISM: ARTIFICIAL SEQUENCE
<220> FEATURE:
<223> OTHER INFORMATION: tag specific oligo 3

<400> SEQUENCE: 10
gtatctgctt atgtcgcccg                                                  20

<210> SEQ ID NO 11
<211> LENGTH: 65
<212> TYPE: DNA
<213> ORGANISM: ARTIFICIAL SEQUENCE
<220> FEATURE:
<223> OTHER INFORMATION: Circularisation Oligo 3

<400> SEQUENCE: 11
gttctgtcat acagtgaatg cgagtccgtc taagagagta gtacagcagc cgtcaagagt      60

```
gtcta                                                             65

<210> SEQ ID NO 12
<211> LENGTH: 19
<212> TYPE: DNA
<213> ORGANISM: ARTIFICIAL SEQUENCE
<220> FEATURE:
<223> OTHER INFORMATION: tag specific detection oligo 1

<400> SEQUENCE: 12
tatctgctta tgtcgcccg                                              19

<210> SEQ ID NO 13
<211> LENGTH: 35
<212> TYPE: DNA
<213> ORGANISM: ARTIFICIAL SEQUENCE
<220> FEATURE:
<223> OTHER INFORMATION: Long circularisation oligo

<400> SEQUENCE: 13
gttctgtcat attaaaaaaa aaataagcgt cttaa                            35

<210> SEQ ID NO 14
<211> LENGTH: 22
<212> TYPE: DNA
<213> ORGANISM: ARTIFICIAL SEQUENCE
<220> FEATURE:
<223> OTHER INFORMATION: detection oligo 1

<400> SEQUENCE: 14
uugtatctgc ttatgtcgcc cg                                          22

<210> SEQ ID NO 15
<211> LENGTH: 22
<212> TYPE: DNA
<213> ORGANISM: ARTIFICIAL SEQUENCE
<220> FEATURE:
<223> OTHER INFORMATION: detection oligo 2

<400> SEQUENCE: 15
uuctagtgct ggatgatcgt cc                                          22

<210> SEQ ID NO 16
<211> LENGTH: 22
<212> TYPE: DNA
<213> ORGANISM: ARTIFICIAL SEQUENCE
<220> FEATURE:
<223> OTHER INFORMATION: detection oligo 3

<400> SEQUENCE: 16
uuagcgatct gcgagaccgt at                                          22
```

MULTIPLEXED PROXIMITY LIGATION ASSAY

SEQUENCE LISTING

The specification incorporates by reference the Sequence Listing filed herewith named "109435-01-2012-05-21_ST25.txt" created Nov. 19, 2013 and having a size of 3405 bytes.

FIELD OF THE INVENTION

The present invention relates to a method for proximity ligation assay. More specifically, the invention relates to multiplexed proximity ligation assay method for the detection of molecular interactions or features on a molecule, or combinations thereof.

BACKGROUND OF THE INVENTION

In-situ PLA (proximity ligation assay) technology was developed by Ulf Landegren et al. (.Söderberg, O., Gullberg, M., Jarvius M. et al, *Nature Methods*, 2006, 3(12): 995-1000)) and commercialized by Olink Biosciences AB (www.olink.se). In-situ PLA offers extreme signal amplification. Via the use of dual recognition events at the primary level, the specificity is highly increased. This detection principle has been applied to interrogation of fixed tissue/cells (immunohistochemistry-like applications) and to a lesser extent protein arrays.

In the standard design, two affinity-binders (antibodies, affibodies, aptamers etc.) are conjugated to sequence-designed oligonucleotides, the combination denoted proximity probes and used to probe a sample (FIG. 1). If and only if the two affinity-binder reagents bind in proximity of each other a paired set of specialized and sequence matched oligonucleotides (i.e. backbone- and splint oligo) can hybridize to the binder-conjugated oligos and be converted to a circular molecule by ligation reactions. Next, rolling circle amplification (RCA) is used to elongate one of the binder-conjugated oligos. As a result, each correctly bound pair of affinity reagents are converted into localized DNA-spheres (~1 μm in diameter, also referred to as rolling circle products or RCPs) containing up to a thousand copies of the circular DNA molecule (engineered to contain binding sites for oligonucleotide reporter probes). The detection is accomplished through hybridization of detection oligos complementary to the RCP. Designs requiring three or more oligo-conjugated affinity-reagents binding in proximity for circularization/RCA have also been reported (Protein Diagnostics by Proximity Ligation: Combining Multiple Recognition and DNA Amplification for Improved Protein Analyses, Leuchowius, K-L., et al., Molecular Diagnostics (Second Edition), 2010, Pages 299-306).

There are several possible implementations of the standard design, for example: (1) A single primary antibody in combination with a pair of two oligo-conjugated secondary antibodies. The secondary antibodies specifically recognize two distinct epitopes of the primary antibody (species specific and/or conjugated haptens such as biotin). (2) Two primary antibodies in combination with a pair of two oligo-conjugated secondary antibodies. Primary antibodies need to be of different species origin or conjugated to different haptens. (3) Two oligo-conjugated primary antibodies.

In situ PLA has been used for localized detection of proteins, protein-protein interactions and post-translational modifications in cells and tissues (O. Söderberg, M. Gullberg, M. Jarvius et al., *Nat Methods* 3 (12), 995-1000 (2006)). Owing to its intrinsic requirement of dual target recognition by pairs of antibodies and the use of rolling circle amplification (RCA) to amplify successful detection events, the assay can attain a very high level of selectivity and sensitivity in the detection of single endogenous proteins or post-translational modifications (M. Jarvius, J. Paulsson, I. Weibrecht et al., *Mol Cell Proteomics* 6 (9), 1500-1509 (2007); K. J. Leuchowius, M. Jarvius, M. Wickström et al., *Mol Cell Proteomics* 9 (1), 178-183 (2010)). The same dual recognition also permits detection of protein-protein interactions by targeting two different proteins in a complex.

Expanding the knowledge of the cellular protein interaction networks is vital for a better understanding of several types of diseases, including cancer. Improved methods to study these interaction networks, especially in clinical material, is therefore of great importance both for increasing the knowledge of the underlying disease mechanics, but also for finding new biomarkers for improved disease diagnostics and treatment response prediction. Another context where multiplexed detection of protein-protein interactions could prove of decisive importance is in the field of network pharmacology, where drugs are designed to act on several drug targets simultaneously. The rationale being that as cellular interaction networks are quite robust because of their underlying structure, to perturb these networks and to avoid escape mutations in malignancy, it may prove crucial to target several proteins simultaneously.

There is a need for new methods that can provide information on more than isolated protein interaction events, such as the simultaneous detection of several interactions. Such methods can help monitor the cellular interaction networks, and provide better diagnostics and treatment options.

SUMMARY OF THE INVENTION

The present invention provides a method for detecting interactions between or with any two of at least three target substrates, or any two of at least three features of a target substrate, or a combination of interactions and features of target substrates, by a multiplexed proximity ligation assay, said method comprising:
  a) for each of the at least three target substrates or features, providing a proximity probe comprising a binding moiety with affinity for the feature or binding site on said substrate, and a proximity probe oligonucleotide coupled on the binding moiety; wherein each of the proximity probe oligonucleotides carries a unique tag sequence (e.g. in the middle, flanked by sequences identical for all the proximity probe oligonucleotides);
  b) mixing the proximity probes with a sample, under a condition to allow binding of each proximity probe to its respective binding site or feature on each of said substrates through the binding moiety,
  c) simultaneous with, or following step b), forming circularized DNA molecules where any two proximity probes bind sufficiently close to each other on the substrate, wherein each of the circularized DNA molecules comprise complementary sequences to the unique tag sequences from the two proximity probes oligonucleotides;
  d) amplifying the circularized DNA;
  e) characterizing the amplified DNA.

The invention provides multiplexed proximity ligation assay methods, which enable the simultaneous in situ visualization of multiple concurrent protein-protein interactions. By modifying the design of oligonucleotide components of the proximity assay, this set-up allows for the simultaneous detection of several interactions, e.g. protein-protein interactions, in the same reaction. The analysis of several concurrent signaling events in individual cells can enable a systems understanding for disease diagnostics and drug discovery.

DETAILED DESCRIPTION OF THE INVENTION

In one embodiment, a tag sequence is introduced in the oligonucleotide portion of each proximity probe, uniquely identifying each probe. These tags are propagated into the single-stranded rolling circle products (RCPs) after a successful detection event where two proximity probes have bound interacting proteins or different modifications of the same protein. This enables deduction of which combinations of proximity probes gave rise to signals, and thus, which proteins interacted, or what modifications are on a protein. The amplified tags in the RCPs can be detected with detection oligonucleotides designed to uniquely report the identity of the different tags by the use of different fluorophores for detection oligonucleotides for each unique tag.

Figure 1:
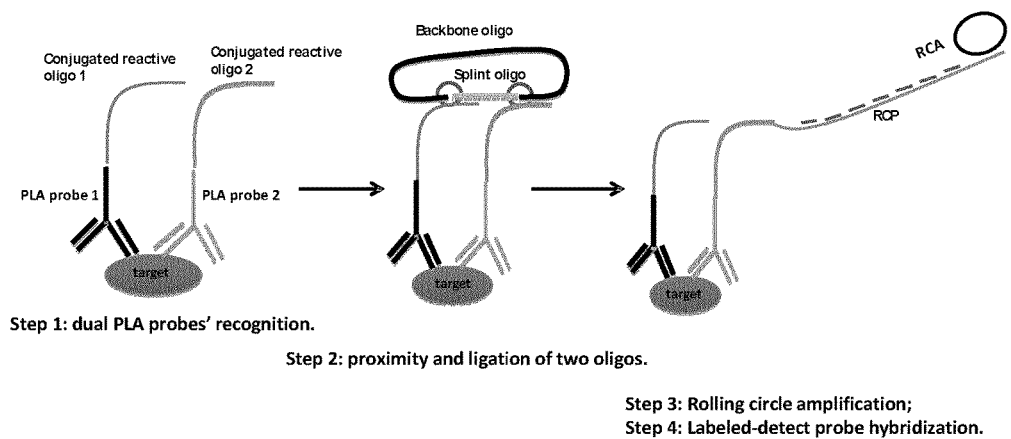
FIG. 1 shows a schematic overview of a prior art standard in situ PLA.
Figure 2:
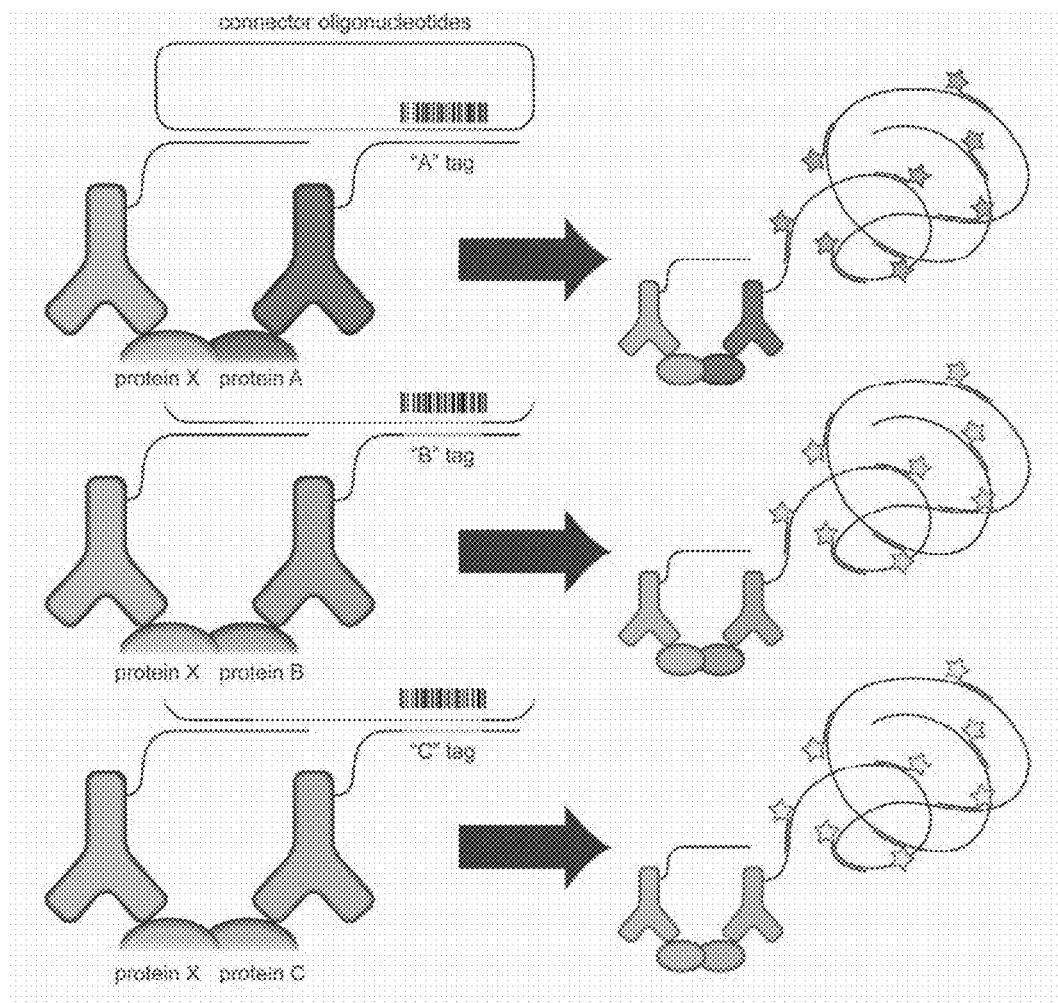
FIG. 2 shows one scheme for the simultaneous detection of combinatorial protein-protein interactions with multiplexed PLA.

This detection scheme can be used in a combinatorial fashion; for instance, by using one common proximity probe in combination with tagged proximity probes targeting three different proteins interacting with the common protein, all the pair-wise interactions between the common protein and the three interacting proteins can be visualized simultaneously (FIG. 2). Using the proximity probes as templates, two linear connector oligonucleotides and a probe-specific tag oligonucleotide can be enzymatically fused into a DNA circle that can be used as a template for rolling circle amplification. The rolling circle products can then be visualized by hybridization of fluorophore-labeled tags (i.e., specific detection oligonucleotides each with a different label) to reveal which proteins interacted.

Figure 3:
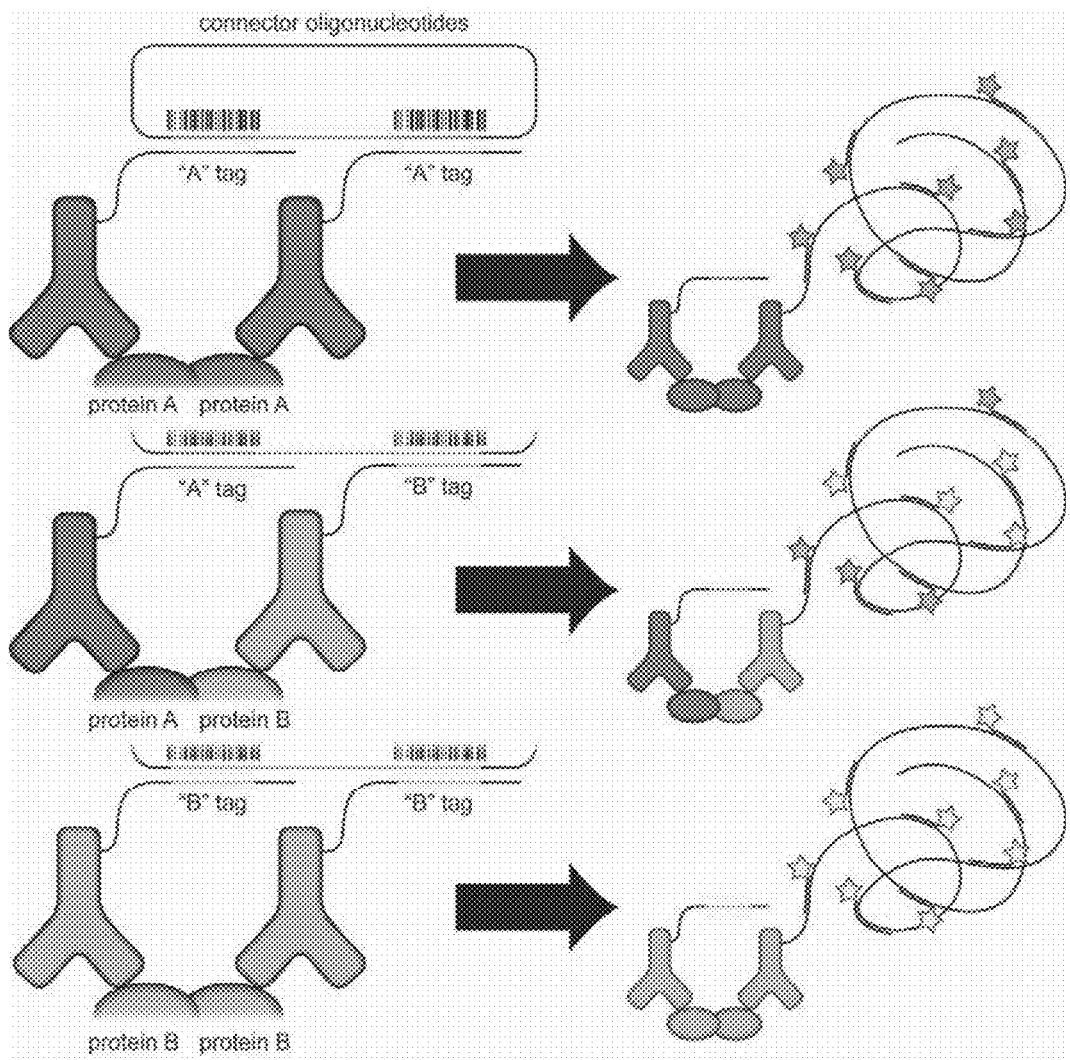
FIG. 3 shows a variation of a scheme for the combinatorial PLA with dual tags.

In a variation of the embodiment, the approach can be used to detect all pairwise interactions among members of a set of target proteins by replacing the common proximity probe with a set of tagged probes and analyzing which pairs of tags co-occur in the RCPs. This is done by using two sets of compatible proximity probes, each tagged with unique DNA sequences. Each detected protein-protein interaction would then introduce two specific tags into the resulting RCP, one for each participating proximity probe. Using tag-specific detection oligonucleotides, the specific tags can then be read out for each RCP, revealing which two proteins interacted (FIG. 3).

For instance, using three different probes targeting three proteins A, B and C, the following interactions could be visualized: AA, AB, AC, BA (same as AB), BB, BC, CA (same as AC), CB (same as BC), and CC. Thus, by using three groups of tagged proximity probes, all the possible interactions between proteins targeted by the three groups of proximity probes can be visualized. The circles formed by two linear common connector oligonucleotides and two probe-specific tag oligonucleotides will contain the identity of the detected interacting proteins, which can be read out from the resulting rolling circle products (RCP). To read out the identities, the tags are decoded by hybridization of tag-specific detection oligonucleotides. The RCP will either be mono-colored, indicating homomeric protein-protein interactions, or duo-colored, indicating heteromeric interactions. The specific colors indicate which proximity probes gave rise to the RCP.

Although the discussions above have used three proteins to illustrate certain aspects of the invention, it is to be understood that the invention is suited for the simultaneous detection of from two to many interactions. With careful design of the oligonucleotide sequences and the combination of different dyes and detection strategies described further below, many more interactions than three pairs can be detected in a multiplexed fashion.

Figure 4:
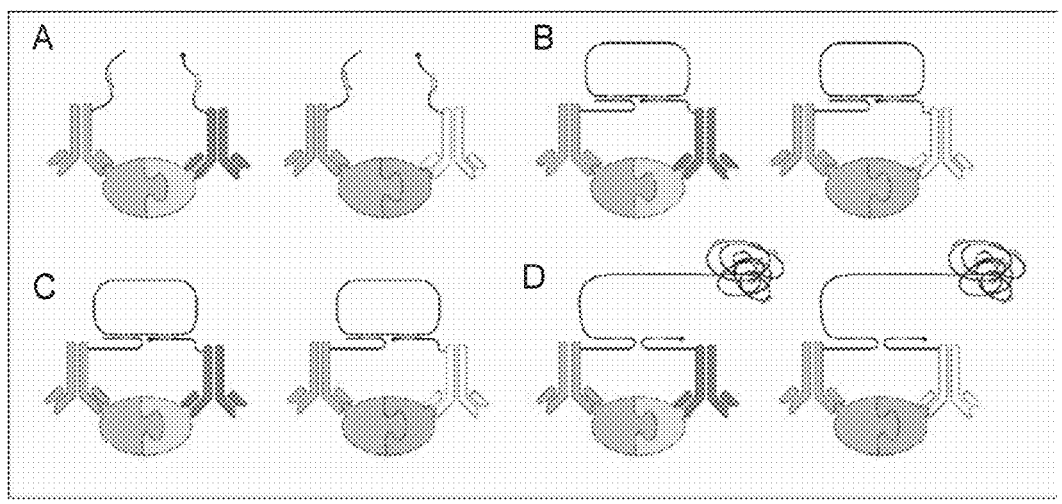
FIG. 4 shows another variation of a scheme for the combinatorial PLA with dual tags, where tagged regions are made double stranded before introduction of the connector probes.

In one variation of the scheme above, the tagged region of the oligonucleotide of each proximity probe is made double stranded before the introduction of the connector probes (FIG. 4A). In this sense it can be seen that a detection oligonucleotide complementary to the unique tag of the proximity probe oligonucleotide is pre-hybridised to the proximity probe oligonucleotide. When the proximity probes bind to their target proteins, their attached oligonucleotide arms will come into proximity of each other and can be used as a template for the ligation to form an oligonucleotide circle (FIG. 4B). The circle formed will consist of a common "backpiece" oligonucleotide and a common "splint" oligonucleotide (the two connector probes), as well as the complement of the specific tagsequences encoded by the proximity probe arms (FIG. 4C). The specificity of the ligation reaction is solely dependent upon the single stranded portion of the oligonucleotide part of the proximity probes, thus all different interaction pairs can be ligated with an equal efficiency, since the single stranded portion of the oligonucleotide part of the proximity probes have the same sequences. An additional advantage is that only addition of two circularization/connector probes is required, independent of the number of interactions assayed. As a result of this, the RCP contains sequences that can be used to identify which proximity probes were used in the formation of it, and thus which interacting proteins were detected (FIG. 4D).

Figure 11:
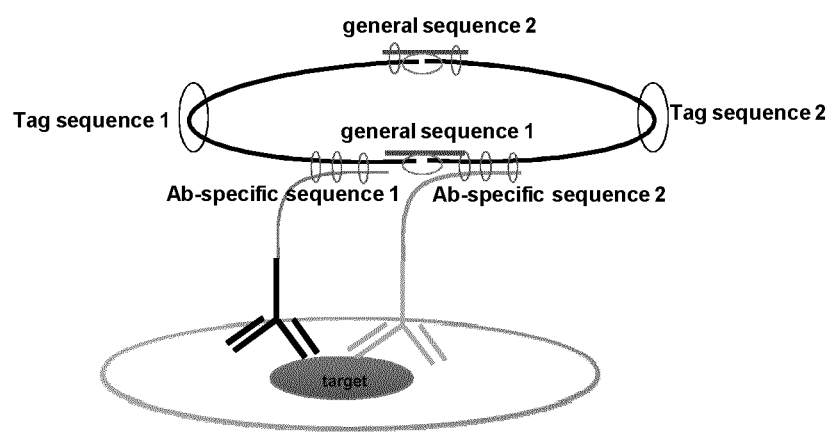
FIG. 11 presents an alternative scheme for the simultaneous detection of combinatorial protein-protein interactions with multiplexed PLA.

As discussed earlier, an identification tag may be used in only one of the proximity probes. In this design, one of the recognized domains will always be the same and the determination of the complementary domain to the first domain is by the tag sequence of the second proximity probe In another aspect of the invention, an alternative design is provided. This design uses an alternative scheme for the connector probes (FIG. 11). Here, two connector probes are used, each unique to a target/proximity probe. Each connector probe contains detection tags outside a proximity probe complementary region. In the context of the method described above, in this alternative embodiment the proximity probe complementary region may be seen as complementary to the unique tag sequence of the proximity probe oligonucleotide, The two connector probes contain regions complementary to proximity probe arms to enable formation of double stranded proximity probes in a first step. The two pieces are then ligated after the addition of two common bridging (splint) oligonucleotides. Hence, only two oligonucleotides are ligated to form the corresponding unique circle. Two detection oligonucleotides are required to identify each unique combination of tags.

Based on this embodiment, in a further aspect, the present invention also provides a method for detecting in a sample a target substrate or for detecting two or more substrates in proximity, by a proximity ligation assay, said target substrate (s) comprising at least two binding sites for at least two proximity probes, said method comprising:

(a) providing at least two proximity probes, each proximity probe comprising a binding moiety capable of directly or indirectly binding to a target substrate and a proximity probe oligonucleotide coupled thereto, wherein said proximity probe oligonucleotide comprises a unique tag sequence which is complementary to, and provides a binding site for, a domain of a connector oligonucleotide;

(b) contacting said sample with said proximity probes under conditions which allow binding of the binding moieties to their respective binding sites on the target substrate (s);

(c) simultaneously or subsequently to step (b), contacting said sample with
  (i) at least two connector oligonucleotides, each connector oligonucleotide comprising an internal domain having a nucleotide sequence which is complementary to and capable of hybridising (in particular hybridising selectively) to a unique tag sequence of a proximity probe oligonucleotide, and a detection tag sequence; and with
  (ii) at least two bridging (i.e. ligation template) oligonucleotides which, when the proximity probes have each bound to their respective target substrate(s) and the connectors have each bound to their respective proximity probe oligonucleotides, are each capable of hybridising to one of each of the respective ends of two connector oligonucleotides, so as to bring the respective ends of two connectors into juxtaposition for ligation directly or indirectly to one another;

(d) ligating said connector ends directly or indirectly to one another to form a circle, (i.e. optionally with a preceding gap filling step if the connector ends are not hybridised immediately adjacent to one another on the bridging oligonucleotide);

(e) detecting and characterising the circle.

Step (e) may advantageously be preceded by a step of amplifying the circle (i.e the circular nucleic acid, or circular DNA). Such amplification may conveniently be by rolling circle amplification, e.g. as described elsewhere herein. Other amplification methods, e.g. PCR may also be used.

Preferably, in step (e) the circle is detected and characterised by means of the detection tags in the connector oligonucleotide, for example by means of detection oligonucleotides which hybridise to the detection tags or to their complements in amplification product of the circle, e.g. labeled detection oligonucleotides, for example with fluorescent labels.

The detection tag sequence of a connector oligonucleotide is capable of identifying that connector and the proximity probe oligonucleotide to which it binds. The detection tag sequence may accordingly be unique to each connector oligonucleotide. It may thus be viewed as an identification tag for the connector, and hence indirectly of the proximity probe to the oligonucleotide of which the connector binds. Accordingly it may be used as the means of identifying the substrate to which the proximity probe binds. Thus, depending on the specificity of the binding moiety, the method may be used to detect a substrate, or a feature of substrate (to which the binding moiety binds) or substrate which is part of a complex or interaction etc. Thus, substrates in proximity, for example as a result of being part of a complex, or of an interaction, or by present in proximity on the same cellular membrane etc. may be detected. In this way the component parts of an interaction may be identified. As described above, this aspect of the invention has particular utility in a multiplex setting, e.g. to detect molecular interactions or features of a molecule etc., or combinations thereof. This method may be used in combinatorial fashion as described in relation to the methods above. For example it may be used to detect interactions between or with any two of at least three target substrates, or any two of at least three features of a target substrate, or a combination of interactions and features of target substrates. In such a method, a proximity probe may be provided for each of the at least three target substrates or features.

Figure 5:
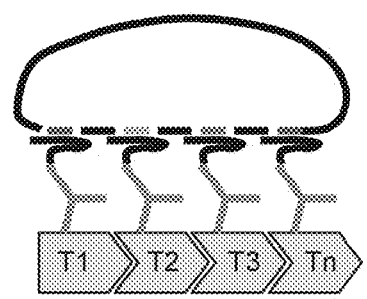
FIG. 5 shows a scheme for a PLA detection of four interactions.

Although the discussions above have focused on the detection of interactions between two proteins or two features (modifications) of a protein, it is to be understood that the invention is suited for the detection of the interaction of more than two proteins, or other targets, or more than two features of a protein or other target, or a combination of more than two proteins, or other targets, and features. Thus, more than two proximity probes can be used for the detection of interactions/features at close proximity. One or more of the participating proximity probes may be equipped with tag sequences. A circular DNA reporter molecule may thus be created in a similar fashion from many proximity probes bound to the same target (FIG. 5).

The limited number of fluorophores that can be used simultaneously without spectral overlap present a hurdle for the limit of multiplexed detection. In one variation of the above design, the sequence of the circular DNA molecule formed in the above approaches can be designed such that secondary structure of corresponding RCPs renders the formation of looped structures in the regions between the two tags. In this way, the two tag regions are close to each other and the two tags can be probed with a single detection oligonucleotide containing two complementary regions with a middle region spacer. Hybridization condition can be controlled such that detection probes hybridizing to only one tag is unstable and will be washed off before detection. One obvious benefit is that only one detection oligonucleotide is needed to detect the interaction of any two binders.

Figure 10:
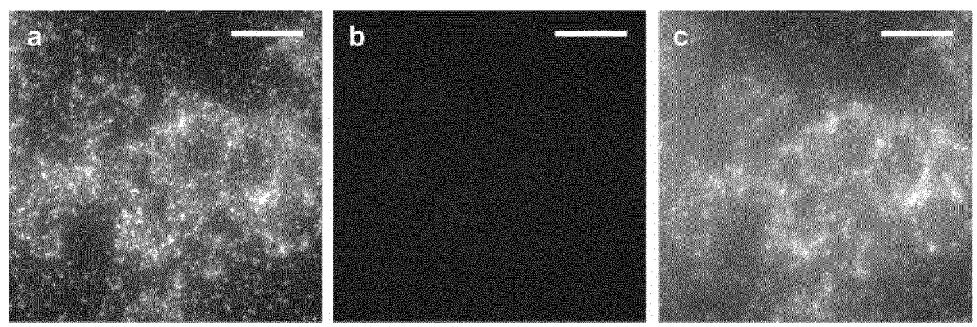
FIG. 10. Serial detection of rolling circle products is performed by removal of detection oligonucleotides followed by rehybridization with new detection oligonucleotides. Shown is the visualization of HER2-HER2 interactions in breast cancer tissue (a) before removal of the detection oligonucleotides, (b) after removal of the detection oligonucleotides, and (c) after rehybridization of the detection oligonucleotides. Scale bars indicate 20 μm. The three images are all from the same tissue area and have been imaged with the same exposure times.

Alternatively, strategies for serial detection of tags or tag complements in RCPs can be used: (1) the detection oligonucleotides can be removed completely after imaging by dislodging the oligonucleotides from the RCP, or (2) the detection oligonucleotides can contain fluorophores which can be cleaved off enzymatically or chemically after imaging. After oligonucleotide removal or fluorophore cleavage, another set of tags or tag complements can then be detected with new detection oligonucleotides, using the same fluorophores as previously used. The process can thus be repeated until all tags or tag complements have been decoded. In this way, the multiplexing ability of the assay can be increased substantially (FIG. 10).

Alternatively, based on the successful application of multiplexed in-situ PLA, another aspect of the invention provides a method for controlling/building localized fluorescent bar-codes based on combinations of target specific RCPs and fluorophore labeled detection oligonucleotides. This enables a procedure for increasing the obtainable multiplexing-level without the need of a high number of fluorophores or the use of stripping methodologies or other repeated probing strategies. In addition the high sensitivity and unique detection specificity offered by PLA can thus be exploited for multiple targets at once, thereby further extending the amount and type of information that can be extracted from scarce samples (isolated stem cells/primary cells, xenograft aspirates and biopsies).

The following features of in-situ PLA may be important to this aspect of the invention:
(1) Fluorophores are administered via detection oligonucleotides. In contrast to antibody labeling this enables precise control over the number of fluorophore molecules per reagent (i.e. one).
(2) A large number of target sequence repeats (~1000) are present (in target specific RCPs) locally for each specifically detected antigen. Hence, variation in actual fluorophore ratios for individual RCPs, due to statistical effects during hybridization, can be kept low.

Figure 12:
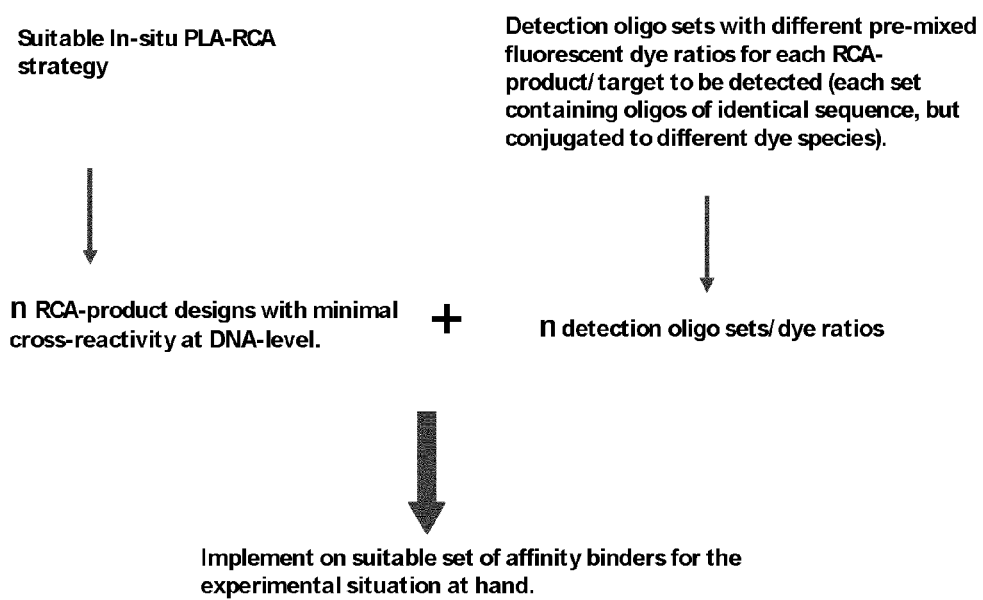
FIG. 12 shows a scheme for detection of an amplification product using ratio-labeled detection oligonucleotides.

Thus, one embodiment of the invention provides a multiplexed in situ PLA method, using unique bar-codes based on defined ratios of two (or more) fluorophores in target specific RCPs (FIG. 12). In this method, oligonucleotide sets for the number of targets to be detected are designed for minimal cross-reactivity during proximity ligation and RCA. Hence, using suitable affinity reagents, target specific RCPs can be generated. Further, each target specific RCP is designed to contain amplified copies of a target specific sequence region which can promote hybridization to a unique detection oligonucleotide sequence. For each RCP a sequence complementary to the unique detection sequence is produced. Each such detection oligonucleotide sequence is conjugated to one or more different fluorescent dyes (in case of multiple dyes, different aliquots of unlabeled oligonucleotides are conjugated to single dyes). For each target substrate/RCP to be detected, defined and unique ratios of the differently labeled detection oligonucleotides (all having identical sequence) are pre-mixed (one mixture for each target substrate/unique RCP). The complete set of detection oligonucleotide mixtures are added to the reaction, and the dye ratios are transferred to localized target specific RCPs via sequence specific hybridization. A fluorescent imager or scanner is used to generate multiple images (one with optimal settings for each dye included) of the sample. De-coding is dependent on proper calibration of signal gains for the different dyes included. For the purpose of image acquisition equipment calibration, a well-defined standard sample (probed using one of the RCP designs used for unknown samples and an equimolar mixture of all the dyes included in the experiment) is tested separately. Following calibration, measured dye ratios can be de-coded. Quantitative analysis is then performed using optimal images for each target.

Figure 13:
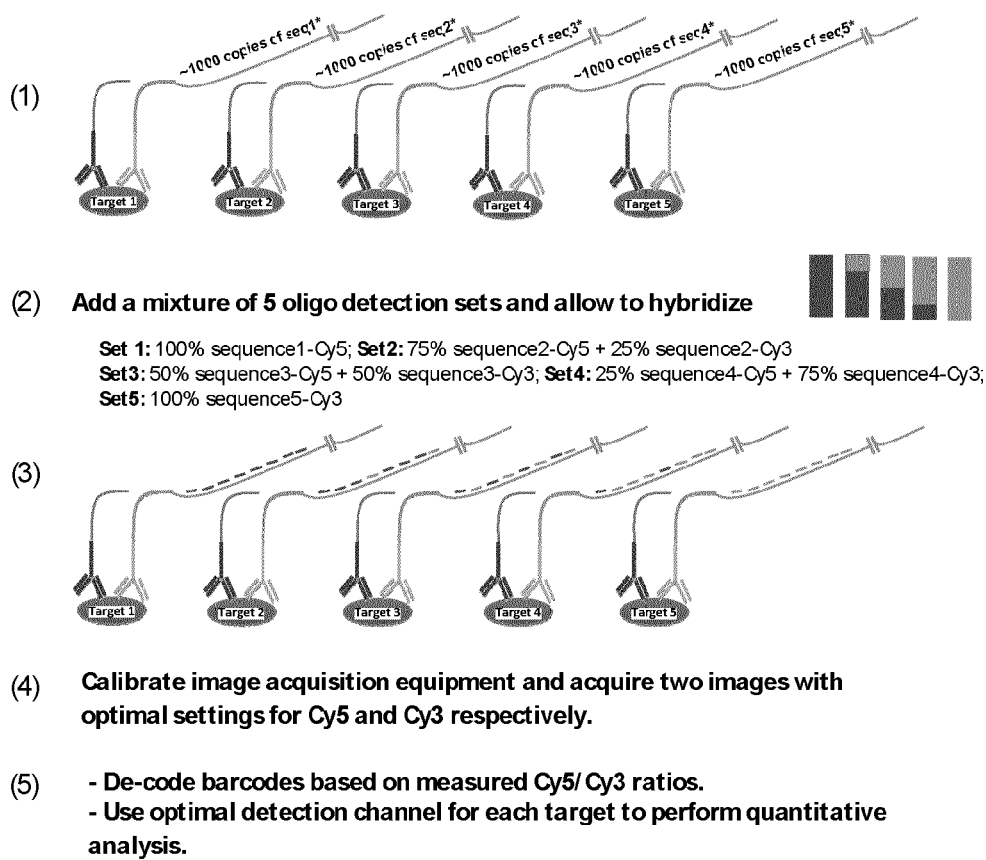
FIG. 13 shows a schematic example of a labeling scheme for a 5-plex proximity ligation assay using detection oligonucleotides "bar-code labeled" with two different fluorescent dyes.

FIG. 13 provides an example of a 5-plex PLA using only CY™3 and CY™5, with localized "bar-codes":
(1) Each target to be analysed is assigned a bar-code based on a defined ratio of CY™5 to CY™3 (only CY™5, 3:1, 1:1, 1:3 and only CY™3). Five PLA reagent sets (each containing two PLA proximity probes and corresponding connector, proximity probe specific tag and detection oligonucleotides) are designed according to the scheme outlined in the general description. Each set recognizes a unique target substrate and generates target specific RCPs (e.g., see FIG. 2), with minimal interference from other sets, following proximity ligation and RCA.
(2) Aliquot(s) of each detection oligonucleotide are labeled with CY™5, CY™3 or both and then mixed in the predetermined CY™5/CY™3 ratio. Thus the group of five detection oligonucleotide sequences are present in the following mixtures: (1) 100% CY™5; (2) 3:1 of CY™5: CY™3; (3) 1:1 of CY™5: CY™3; (4) 1:3 of CY™5: CY™3; and (5) 100% CY™3; respectively.
(3) Detection oligonucleotides for the five substrates are mixed together, added to the reaction and thereby transferred to corresponding local RCPs via sequence-specific hybridization.
(4) A suitable image acquisition equipment is used to generate images with optimal settings for CY™5 and CY™3, respectively. Calibration of CY™5 to CY™3 signal gain is achieved via the procedure outlined in the general description (using a separate standard sample).
(5) The "barcodes" are decoded based on the signal gain calibration and measured CY™5:CY™3 ratios. Furthermore, optimal detection channels are used for each target to perform quantitative analysis (channel/image with highest signal to noise chosen for each target/barcode).

Thus, as shown in FIG. 13, following proximity ligation and RCA each unique target substrate (e.g., protein modification or protein complex) can be detected using an oligonucleotide the sequence of which corresponds to a complementary sequence of the corresponding RCP. The oligonucleotides are labeled with either CY™5 or CY™3, but the combined oligonucleotides pool for each target has a predetermined ratio of CY™5 and CY™3. The oligonucleotide pool of oligonucleotides for each target has a ratio of CY™5 and CY™3 distinguishable from the ratios of other oligonucleotides pools. Thus, multiplexing is achieved. Although FIG. 13 presents an example with two dyes, it could be advantageous in certain circumstances to use more than two dyes. The principle is similar nonetheless.

An optimized set of bar-code oligonucleotide sets as outlined above can be transferred to any desired set of antibodies (or other affinity reagents) and used in different assay set-ups. To reach really high multiplexing, oligonucleotide conjugation needs to be performed at the primary binder level due to the limited number of different sources (species) of antibodies available. However, the principle can also be applied to secondary detection formats. For example to design a 5-plex secondary kit using only two fluorophores.

In certain embodiments, the binding moieties are antibodies and the antibodies each bind to the substrate via one or two further antibody/antibodies having binding specificity for the substrate, and wherein the binding moieties are directed against the Fc portion and/or conjugated haptens of the further antibody/antibodies. The term antibody is used broadly herein to include any antibody fragment or derivative. A number of such fragments (e.g. Fab, Fab'. Fv fragments etc.) and derivatives are known and describe in the art, e.g. single chain antibodies, chimeric antibodies etc.

In other embodiments, the binding moieties are selected from a protein, such as a monoclonal or polyclonal antibody, lectin, soluble cell surface receptor, combinatorially derived protein from phage display or ribosome display, peptide, carbohydrate, nucleic acid, such as an aptamer, or combinations thereof. It will be seen that any affinity binding molecule may be used.

The design and preparation of proximity probes is widely described in the art, for example various different binding moieties which may be used, the design of proximity probe oligonucleotides for proximity ligation assays, and the coupling of such oligonucleotides to the binding moieties to form the probes. The details and principles described in the art may be applied to the design of the proximity probes for use in the methods of the invention. For example reference may be made to WO 2007/107743, U.S. Pat. Nos. 7,306,904 and 6,878,515 of Olink AB which are incorporated herein by reference.

Multiplexed assays as demonstrated here save time and effort, as well as precious clinical material. More importantly, the ability to simultaneously assess multiple concurrent molecular events within the same cells can provide entirely new opportunities to elucidate the intricate networks of protein interactions within cells. Multiplexed in situ PLA can be used to measure and quantify the balance between alternative protein interactions for a systems understanding of cellular functions.

EXAMPLES

The invention will now be more fully described in association with some examples which are not to be construed as limiting for the invention.

Materials and Methods

Preparation of Proximity Probes

For the combinatorial detection of multiple protein-protein interactions simultaneously, proximity probes for each target protein were created by covalently attaching oligonucleotides containing antibody-specific DNA tags to the corresponding antibodies. For each type of antibody, a general proximity probe was also created. In contrast to the other proximity probes, the β-catenin probe was created by attaching the antibody to the 3'-end of the oligonucleotide instead of the 5'-end. The conjugated antibodies and oligonucleotides are described in Table 1. The conjugation procedure was performed essentially as described by K. J. Leuchowius, I. Weibrecht, U. Landegren et al., *Cytometry A* 75 (10), 833-839 (2009); however, to increase the conjugation efficiency, we replaced the MES conjugation buffer with a phosphate buffer (100 mM phosphate, 150 mM NaCl, pH 6.0). In addition, 10 mM aniline (Sigma-Aldrich) was included as a catalyst in the conjugation reaction. All conjugates were purified by HPLC on a Superdex-75 column (GE Healthcare, Sweden) to remove unreacted oligonucleotides and aniline.

TABLE 1

Antibodies and oligonucleotides used to create the proximity probes
Supplementary Table 1: Antibodies and oligonucleotides used to create the proximity probes

| Proximity probe | Antibody | Oligonucleotide | SEQ ID NO |
|---|---|---|---|
| EGFR general | EGFR Ab-15 (Labvision) | 5'-aldehyde-GAC GCT AAT AGT TAA GAC GCT T | 1 |
| EGFR specific | EGFR Ab 15 (Labvision) | 5'-aldehyde-AAA AAA AAA ATA TGA CAG AAC CGG GCG ACA TAA GCA GAT ACT AGA CAC TCT T | 2 |
| HER2 general | HER2 Ab- 8 (Labvision) | 5'-aldehyde-GAC GCT AAT AGT TAA GAC GCT T | 1 |
| HER2 specific | HER2 Ab- 8 (Labvision) | 5'-aldehyde-AAA AAA AAA ATA TGA CAG AAC ATA CGG TCT CGC AGA TCG CTT AGA CAC TCT T | 3 |
| HER3 general | HER3 Ab-2 (Labvision) | 5'-aldehyde-GAC GCT AAT AGT TAA GAC GCTT | 1 |

TABLE 1-continued

Antibodies and oligonucleotides used to create the proximity probes
Supplementary Table 1: Antibodies and oligonucleotides used to
create the proximity probes

| Proximity probe | Antibody | Oligonucleotide | SEQ ID NO |
|---|---|---|---|
| HER3 specific | HER3 Ab-2 (Labvision) | 5'-aldehyde-AAA AAA AAAATA TGA CAG AAC GGA CGA TCA TCC AGC ACT AGT AGA CAC TCT T | 4 |
| β-catenin general | Anti-β-catenin, clone BDI109 (GenWay) | 5'-AGA CGC TAA TAG TTA AGA CGC TTA UUU-aldehyde, U = uracil | 5 |
| E-cadherin specific | Anti-E-cadherin, clone 36 (BD Biosciences) | 5'-aldehyde-AAA AAA AAA ATA TGA CAG AAC ATA CGG TCT CGC AGA TCG CTT AGA CAC TCT T | 3 |
| TCF1 specific | Anti-TFC1, clone 7H3 (Thermo Scientific) | 5-aldehyde-AAA AAA AAA ATA TGA CAG AAC CGG GCG ACA TAA GCA GAT ACT AGA CAC TCT T | 2 |

All oligonucleotides were purchased from TriLink Biotechnologies.

Cell Cultures and Fresh Frozen Tissue

A selection of cell lines stably transfected with different combinations of EGFR, HER2 and HER3 were cultivated according to published protocols by N. M. Pedersen, K. Breen, M. S. Rodland et al., *Mol Cancer Res* 7 (2), 275-284 (2009). Before use in the in situ PLA reactions, the cells were seeded on Lab-Tek II chamber slides (Thermo Fisher Scientific Nunc) over night, then washed with PBS and fixed with ice-cold 70% ethanol for 60 minutes. Fully anonymized fresh frozen human tissue sections were obtained from the Fresh Tissue Biobank at the Department of Pathology, Uppsala University Hospital, in accordance with the Swedish Biobank Legislation. The breast cancer tissue sections had previously been characterized by HercepTest (Dako) and received a score depending on the amount of HER2 protein staining (varying between 0+ indicating no detectable staining, to 3+ indicating strong staining intensity). Before use, the frozen breast cancer tissues were removed from the storage at −80° C. and fixed in ice-cold 70% ethanol for 60 minutes then dried. The frozen colorectal cancer tissues were removed from the storage at −80° C. and fixed in ice-cold 1% paraformaldehyde for 30 minutes, permeabilized with 70% ethanol for 15 minutes, then dried.

Multiplexed Quantification of Interactions Between EGFR, HER2 and HER3 in Cultured Cells and Fresh Frozen Breast Cancer Tissues To reduce the likelihood of unspecific binding of proximity probes, the fixed cells and tissues on glass slides were first incubated with a blocking solution (1× TBS with 10% sterile filtered goat serum and 2.5 ng/µl sonicated salmon sperm DNA) for 60 minutes at 37° C. The proximity probes were then diluted 1:50 in blocking solution with 0.05% Tween-20 added, and applied to the slides for an overnight incubation at 4° C. After the incubation, the slides were washed three times for five minutes with TBST (1× TBS with 0.05% Tween-20) to remove unbound probes.

Hybridization and ligation of linear oligonucleotides into DNA circles was performed by incubating the slides with 125 nM circularization oligonucleotides (5'-phosphate-CTA TTA GCG TCC AGT GAA TGC GAG TCC GTC TAA GAG AGT AGT ACA GCA GCC GTC AAG AGT GTC TA (SEQ ID NO: 6) and 5'-phosphate-GTT CTG TCA TAT TTA AGC GTC TTA A (SEQ ID NO: 7), both from Integrated DNA Technologies) and 125 nM tag-specific oligonucleotides (5'-phosphate-AGC GAT CTG CGA GAC CGT AT (SEQ ID NO: 8), 5'-phosphate-CTA GTG CTG GAT GAT CGT CC (SEQ ID NO: 9), 5'-phosphate-GTA TCT GCT TAT GTC GCC CG (SEQ ID NO: 10), all from Integrated DNA Technologies) in ligation buffer (10 mM Tris-acetate, pH 7.5, 10 mM magnesium-acetate, 50 mM potassium-acetate, 250 mM NaCl, 0.25 µg/µl BSA, 0.05% Tween-20, and 1 mM ATP (Fermentas)) with 0.05 unit/µl T4 DNA ligase (Fermentas) for 30 minutes at 37° C. For the cell lines, as the proximity probes were tested one at a time, the two circularization oligonucleotides were replaced by a single circularization oligonucleotide (5'-phosphate-GTT CTG TCA TAC AGT GAA TGC GAG TCC GTC TAA GAG AGT AGT ACA GCA GCC GTC AAG AGT GTC TA (SEQ ID NO:11), from Integrated DNA Technologies) at a concentration of 125 nM. The slides were washed twice for 5 minutes with TBST.

Rolling circle amplification of the DNA circles was performed by incubating the slides with RCA buffer (33 mM Tris-acetate pH 7.9, 10 mM magnesium-acetate, 66 mM potassium-acetate, 0.1% Tween-20, 1 mM DTT, 0.25 µg/µl BSA, and 250 µM dNTP (Fermentas)) with 0.125 unit/µl phi-29 DNA polymerase (Fermentas) for 100 minutes at 37° C. The slides were washed twice for five minutes with TBST. To detect the rolling circle products, the slides were incubated with 25 mM tag-specific detection oligonucleotides (5'-Alexa 488-TAT CTG CTT ATG TCG CCC G (SEQ ID NO: 12), 5'-Cy5-CTA GTG CTG GAT GAT CGT CC (SEQ ID NO: 9), 5'-Alexa 555-AGC GAT CTG CGA GAC CGT AT (SEQ ID NO: 8), all from Integrated DNA Technologies) in hybridization buffer (1× SSC, 0.25 µg/µl BSA, and 0.05% Tween-20) with 1 µM Hoechst 33342 (Sigma) for 60 minutes at 37° C. Finally, the slides were washed twice for ten minutes with a final wash buffer (400 mM Tris-HCl with 200 mM NaCl, pH 7.5) and quickly dipped in 0.1× final wash buffer before they were dried by centrifugation, and mounted with Vectashield (Vector Labs).

Images of cultured cells were acquired using an Axioplan II epifluorescence microscope (Zeiss) equipped with a 100 W mercury lamp, a cooled CCD camera (AxioCam HRm, Zeiss), and a computer-controlled filter wheel with excitation and emission filters for visualization of DAPI, FITC, Cy3, Cy3.5 and Cy5. A ×20 (Plan-Apochromat, Zeiss) or a ×40 (Plan-Neofluar, Zeiss) objective was used for capturing the images. Images were collected as Z-stacks using the AxioVision software (release 4.8, Zeiss) and merged by maximum intensity projection. Image analysis and RCP quantification was performed with the open-source cell image analysis software CellProfiler (A. E. Carpenter, T. R. Jones, M. R. Lamprecht et al., *Genome Biol* 7 (10), R100 (2006)).

Multiplexed Quantification Of Interactions Between β-catenin And E-cadherin in Fresh Frozen Colorectal Cancer Tissues The detection of interactions between β-catenin and E-cadherin or TCF1 was performed essentially as for the detection of EGFR-HER2-HER3 interactions described above, but using 0.25 mg/ml of BSA instead of goat serum in the blocking- and proximity probe-incubation solutions. The short circularization oligonucleotide was replaced by a longer version (5'-GTT CTG TCA TAT TAA AAA AAA AAT AAG CGT CTT AA (SEQ ID NO: 13), from Integrated DNA Technologies), and the detection oligonucleotides were replaced by two other detection oligonucleotides (5'-Alexa 488-AGC GAT CTG CGA GAC CGT AT (SEQ ID NO: 8), 5'-Texas Red-GTA TCT GCT TAT GTC GCC CG (SEQ ID NO: 10), from Integrated DNA Technologies).

Results and Discussion:

The epidermal growth factor receptor (EGFR) family consists of four transmembrane tyrosine kinase receptors (EGFR, HER2, HER3 and HER4), and is involved in the regulation of fundamental cellular functions such as cell growth, survival, death, differentiation and proliferation. Increased expression or aberrant regulation of the receptors has been implicated in a range of human malignancies, including breast cancer, where overexpression of HER2 is associated with poor prognosis. Members of the EGFR family can interact in different constellations, with HER2 as the preferred interaction partner (R. Pinkas-Kramarski, L. Soussan, H. Waterman et al., *EMBO J* 15 (10), 2452-2467 (1996)), activating several signaling pathways. Measurement of the expression levels of the different receptor proteins has proven of limited prognostic value, however, and the focus of interest has shifted towards measuring receptor interactions. Methods such as FRET-based detection (G. Brockhoff, P. Heiss, J. Schlegel et al., *Cytometry* 44 (4), 338-348 (2001)) or the VeraTag assay (C. Desmedt, J. Sperinde, F. Piette et al., *Diagn Mol Pathol* 18 (1), 22-29 (2009)) have been proposed. However, the former is difficult to use with clinical material and has a very limited multiplexing capability due to the lack of spectrally compatible FRET-pairs, while the latter is unable to provide localized detection of the interactions, and thus cannot distinguish between cancer cells and surrounding stroma.

Here multiplexed in situ PLA is used to detect interactions between the EGFR family members EGFR, HER2 and HER3 in fresh-frozen human breast cancer tissue. To verify the selectivity of the proximity probes, stably transfected PAE cells expressing different combinations of EGFR, HER2 and HER3 were used, demonstrating selective binding by all proximity probes (data not shown).

Figure 6:
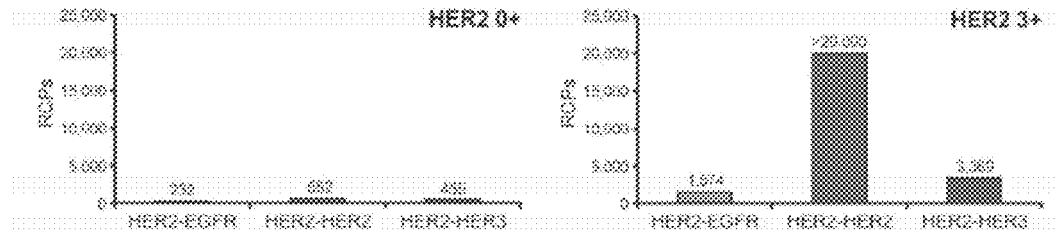
FIG. 6. Visualization of protein-protein interactions by combinatorial in situ PLA. The quantification of the number of in situ PLA signals (RCPs) per image is shown for the interactions between HER2-EGFR, HER2-HER2 and HER2-HER3 in fresh frozen breast cancer tissues. The tissues were previously classified by HercepTest as 0+ (left), indicating no visible HER2 staining, or 3+ (right), indicating strong HER2 staining.

The breast cancer tissues had previously been characterized by immunohistochemistry to assess HER2 expression. The samples were scored either as 0+, indicating no visible staining, or as 3+, indicating strong staining. In the PLA tests, a HER2-specific proximity probe was used in combination with EGFR, HER2 and HER3-specific probes to evaluate the level of interaction of HER2 with all three other receptors. Very high levels of HER2-interactions were observed, especially between HER2 homodimers, in certain areas of the 3+ tissue, corresponding to cells with high levels of HER2 expression (FIG. 6). In the 0+ tissues, no such areas could be found.

Figure 7:
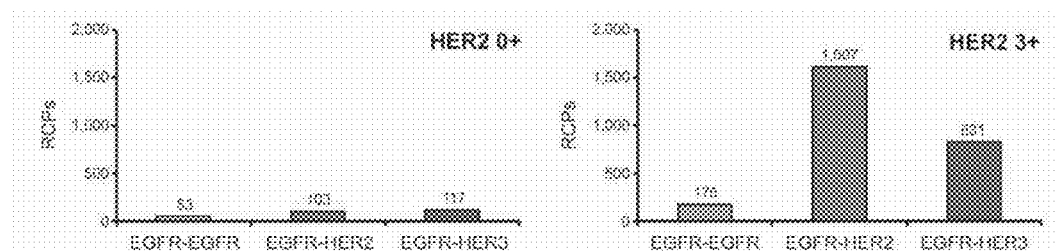
FIG. 7. visualization of EGFR-interactions in breast cancer tissues by combinatorial in situ PLA. The quantification of the number of in situ PLA signals (RCPs) per image is shown for the interactions between EGFR-EGFR, EGFR-HER2 and EGFR-HER3. The tissues were previously classified by HercepTest as 0+ (left), indicating no visible HER2 staining, or 3+ (right), indicating strong HER2 staining.
Figure 8:
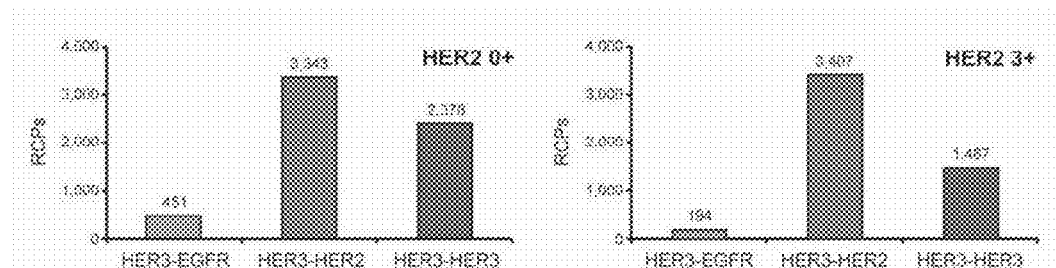
FIG. 8. Visualization of HER3-interactions in breast cancer tissues by combinatorial in situ PLA. The quantification of the number of in situ PLA signals (RCPs) per image is shown for the interactions between HER3-EGFR, HER3-HER2 and HER3-HER3. The tissues were previously classified by HercepTest as 0+ (left), indicating no visible HER2 staining, or 3+ (right), indicating strong HER2 staining.

We also replaced the HER2-specific general proximity probe with probes recognizing EGFR or HER3 to detect all the interactions between EGFR or HER3 with EGFR, HER2 and HER3 (FIGS. 7 and 8, respectively). The amount of interactions involving EGFR and HER3 was generally moderate to low in both tissues, with heterogeneous staining patterns, although not as clearly defined as with the interactions involving HER2.

To show that multiplexed in situ PLA is a general and convenient approach for multiplexed protein interaction analysis, we have also used it to visualize interactions between β-catenin/E-cadherin and β-catenin/TCF1 in fresh-frozen colorectal cancer and normal colon tissues. The canonical WNT signaling pathway is known to have an important role in carcinogenesis and is implicated in the pathogenesis of several tumor types such as colon and breast cancer. In benign cells, most of the β-catenin molecules are transcriptionally inactive and localize at the plasma membrane associated with E-cadherin. Upon canonical WNT activation, β-catenin accumulates in the cytoplasm and then translocates into the nucleus where it interacts with T-cell factor/lymphoid enhancer factor (TCF/LEF) transcription factors to initiate transcription of target genes.

Figure 9:
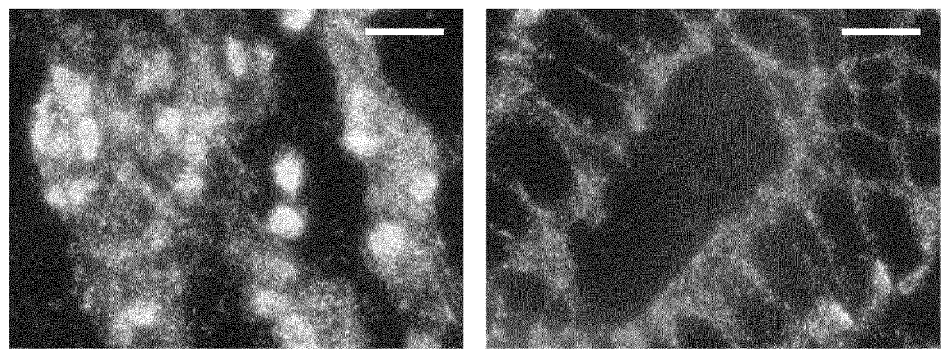
FIG. 9. Visualization of interactions between β-catenin and TCF1 (red), and β-catenin and E-cadherin (green), in colorectal cancer tissue (left) and normal colon epithelium (right). Scale bars indicate 20 μm. Cell nuclei are shown in gray (a) or blue (b).

Using multiplexed in situ PLA for the visualization of the two protein pairs, we successfully observed the expected distinct shift from β-catenin/E-cadherin interactions in the cytoplasm of benign colonic epithelium towards β-catenin/TCF1 interactions in cancer cell nuclei (FIG. 9).

The interaction detection stringency of in situ PLA can be increased by decreasing the maximum distance allowed between a pair of bound proximity probes to generate a signal. One way to do this is to change the design of the oligonucleotides attached to the antibodies. In the case of the β-catenin detection presented here, the oligonucleotide of the common proximity probe was connected to the antibody via the 3'-end of the oligonucleotide instead of the 5'-end (See Materials and Methods). This ensures that the two proximity probes must be in much closer proximity to generate a signal than with the original design. We included three uracil nucleotides in the oligonucleotide at the 3'-end, in case the oligonucleotide needed to be cleaved off the proximity probe by UDG/FPG-treatment after the ligation step, as not to provide steric hindrance during rolling circle amplification. However, it was evident that RCA could be performed successfully without cleaving off the oligonucleotide first.

Serial Detection of RCPs by Removal and Rehybridization of Detection Oligonucleotides The multiplexed in situ PLA reaction was performed as described in Materials and Methods. After fluorescence microscopy, the mounting medium, cover glass and detection oligonucleotides were removed by heating the microscopy slide to 65° C. for one minute, then rinsing the slide in 70% ethanol. To ensure that all detection oligonucleotides had been removed, the slide was washed in TBS for five minutes. It was then mounted with VectaShield and examined in the microscope at the same location as before. After microscopy, the slide was once again heated to 65° C. for one minute, rinsed with 70% ethanol and washed in TBS for five minutes to remove the mounting medium. The last step of the in situ PLA reaction, i.e. hybridization of detection oligonucleotides to the RCPs, was performed again, before the slide was washed and mounted. The slide was then imaged by fluorescence microscopy once more at the same location as before (results shown in FIG. 10).

Enzymatic Cleavage of Tag-Specific Detection Oligonucleotides

The multiplexed in situ PLA reaction was performed as described in Materials and Methods. However, the following detection oligonucleotides were used (5'-Texas Red-UUG TAT CTG CTT ATG TCG CCC G (SEQ ID NO: 14), 5'-Texas Red-UUC TAG TGC TGG ATG ATC GTC C (SEQ ID NO: 15), 5'-Texas Red-UUA GCG ATC TGC GAG ACC GTA T (SEQ ID NO: 16), U=uracil, all from Integrated DNA Technologies). After fluorescence microscopy, the mounting medium and cover glass were removed. The cells were washed in TBS, and then incubated with a cleavage buffer (20 mM Tris-HCl pH 8.2, 1 mM EDTA, 10 mM NaCl, 0.2 mg/ml BSA, 0.05 units/µl UDG Fermentas), 0.2 units/µl FPG (New England Biolabs)) for one minute at 37° C. to remove the uracils, and thus the fluorophores, from the detection oligonucleotides. After washing the slides twice in TBS for five minutes, the slides were incubated with new detection oligonucleotides of different sequences. Results were similar to those obtained by the oligonucleotide removal-rehybridization strategy described above.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A method for detecting interactions between or with any two of at least three target substrates, or any two of at least three features of a target substrate, or a combination of interactions and features of target substrates, by a multiplexed proximity ligation assay, said method comprising:

a) for each of the at least three target substrates or features, providing a proximity probe comprising a binding moiety with affinity for the feature or a binding site on said substrate, and a proximity probe oligonucleotide coupled on the binding moiety, wherein each of the proximity probe oligonucleotides carries a unique tag sequence;

b) mixing the proximity probes with a sample under a condition to allow binding of each proximity probe to its respective binding site or feature through the binding moiety, c) simultaneous with, or following step b), forming respective circularized DNA molecules where any two proximity probes bind sufficiently close to each other, wherein each of the circularized DNA molecules comprises complementary sequences to the unique tag sequences from the oligonucleotides of the two proximity probes forming the circularized DNA molecule;

d) amplifying each circularized DNA molecule; and e) for each amplified DNA, detecting the respective combination of the two unique tag sequences in the amplified DNA, the detected respective combination of two unique tag sequences indicating the two target substrates and/or features to which the two proximity probes forming the respective circularized DNA molecule bound in step (b).

2. The method of claim 1, wherein the unique tag sequence of each proximity probe oligonucleotide is flanked by sequences which are identical for all the proximity probe oligonucleotides.

3. The method of claim 1, wherein the binding moieties are selected from a monoclonal or polyclonal antibody, a protein other than a monoclonal or polyclonal antibody, lectin, soluble cell surface receptor, combinatorially derived protein from phage display or ribosome display, peptide, carbohydrate, aptamer, a nucleic acid other than an aptamer, or combinations thereof.

4. The method of claim 1, wherein the binding moieties are antibodies and said antibodies each bind to said substrate via one or two further antibodies having binding specificity for the substrate, and wherein the binding moieties are directed against the Fc portion or conjugated haptens of the one or two further antibodies.

5. The method of claim 1, wherein the circularized DNA is amplified by isothermal amplification.

6. The method of claim 1, wherein the circularized DNA is amplified by rolling circle amplification.

7. The method of claim 6, wherein said amplification is performed using Phi29 DNA polymerase.

8. The method of claim 1, wherein the circularized DNA is amplified by PCR.

9. The method of claim 1, wherein the circularized DNA is formed by a method comprising:
(i) providing an oligonucleotide complementary to the unique tag sequence for each of the proximity probe oligonucleotides;
(ii) providing two connector oligonucleotides, each carrying sequences at its ends which are complementary to sequences of the proximity probe oligonucleotides outside of the unique tag sequence;
(iii) mixing the oligonucleotides from step (i) and (ii) with the reaction mixture of step b) under conditions to allow hybridization of the oligonucleotides from (i) and (ii) with the proximity probe oligonucleotides; and
(iv) filling in any gaps and ligating the oligonucleotides.

10. The method of claim 1, wherein the circularized DNA is formed by a method comprising:
(i) providing an oligonucleotide complementary to the unique tag sequence for each of the proximity probe oligonucleotides;
(ii) mixing the oligonucleotides from step (i) with the reaction mixture of step b) under conditions to allow hybridization of the oligonucleotides from (i) with the proximity probe oligonucleotides;
(iii) providing two connector oligonucleotides, each carrying sequences at its ends which are complementary to the sequences of the proximity probe oligonucleotides outside of the unique tag sequence;
(iv) mixing the oligonucleotides from step (iii) with the reaction mixture of step ii) under conditions to allow hybridization of the oligonucleotides from (iii) with the proximity probe oligonucleotides; and
(v) filling in any gaps and ligating the oligonucleotides.

11. The method of claim 1, wherein the circularized DNA is formed by a method comprising:
(i) providing two connector oligonucleotides, each carrying an internal domain having a nucleotide sequence complementary to the unique tag sequence for each of the proximity probe oligonucleotides, wherein said connector oligonucleotides each comprise a detection tag sequence;
(ii) providing two bridging oligonucleotides, each carrying sequences which are complementary to and capable of hybridising to one of each of the respective ends of the two connector oligonucleotides; and
(iii) mixing the oligonucleotides of (i) and (ii) with the reaction mixture of step (b) under conditions which allow hybridisation of the connector oligonucleotides of (i) to the proximity probe oligonucleotides and the bridging oligonucleotides of (ii) to the connector oligonucleotides, such that the respective ends of the two connector oligonucleotides are brought into juxtaposition for ligation, directly or indirectly, to one another; and
(iv) if necessary, filling in any gaps between the hybridised connector ends, and ligating the oligonucleotides.

12. The method of claim 11, wherein each detection tag sequence is capable of identifying the respective connector oligonucleotide, and wherein the unique tag sequences are detected by means of the detection tags of the connector oligonucleotides.

13. The method of claim 12, wherein detection oligonucleotides are included and each hybridizes to a complement in the amplified product of a respective detection tag sequence of a connector oligonucleotide.

14. The method of claim 1 wherein step e) comprises
(i) providing a distinctively labeled detection oligonucleotide complementary to each unique tag sequence;
(ii) pooling the labeled detection oligonucleotides for all the target substrates or features and hybridizing the detection oligonucleotides with the amplified products; and
(iii) for each amplified DNA, detecting the labels of the hybridized detection oligonucleotides to thereby detect the respective combination of the two unique tag sequences.

15. The method of claim 14, wherein said detection oligonucleotides are fluorescently labeled and the detection is performed by fluorescence read-out.

16. The method of claim 14, wherein said detecting step is performed by taking multiple scans/images at different excitation wavelength/emission filter combinations.

17. The method of claim 14, wherein said detecting step is performed by multi-spectral imaging by recoding complete emission spectra in each pixel.

18. The method of claim 1, wherein step e) comprises
(i) for each combination of proximity probe pairs, providing a single detection oligonucleotide complementary to both unique tag sequences in the amplified DNA product;
(ii) labeling each type of detection oligonucleotide with a distinctive label,
(iii) pooling the labeled detection oligonucleotides for all the combinations of proximity probe pairs and hybridizing the detection oligonucleotides with the amplified products; and
(iv) for each amplified DNA, detecting the label of the hybridized detection oligonucleotide to thereby detect the respective combination of the two unique tag sequences.

19. The method of claim 13 wherein the detection oligonucleotides are labeled.

20. The method of claim 13 wherein the detection oligonucleotides are fluorescently-labeled.

21. The method of claim 11, wherein step e) comprises
(i) providing a distinctively labeled detection oligonucleotide complementary to each unique tag sequence or to a complement of each detection tag sequence;
(ii) pooling the labeled detection oligonucleotides for all the target substrates or features and hybridizing the detection oligonucleotides with the amplified products; and
(iii) for each amplified DNA, detecting the labels of the hybridized detection oligonucleotides to thereby detect the respective combination of the two unique tag sequences.

* * * * *